United States Patent [19]

Stang

[11] Patent Number: 5,160,185

[45] Date of Patent: Nov. 3, 1992

[54] INFANT SUPPORT AND RESTRAINT SYSTEM

[76] Inventor: Howard J. Stang, 5222 Lakeview Ct., White Bear Lake, Minn. 55110

[21] Appl. No.: 668,222

[22] Filed: Mar. 12, 1991

[51] Int. Cl.$^5$ .............................................. A61G 13/00
[52] U.S. Cl. ..................................... 297/377; 297/466; 297/433; 5/603; 5/618
[58] Field of Search ............... 297/377, 433, 466, 464; 5/618, 655, 603

[56] References Cited

U.S. PATENT DOCUMENTS

| | | | |
|---|---|---|---|
| 5,100 | 5/1847 | Latourondais | 5/618 |
| 2,208,945 | 1/1940 | Miller | 297/377 |
| 2,766,463 | 10/1956 | Bendersky | 297/433 |
| 2,777,138 | 1/1957 | Gallagher | 297/377 |
| 3,211,495 | 10/1965 | Nielsen | 297/377 |
| 3,220,767 | 11/1965 | Hendrickson | 297/DIG. 6 |
| 3,358,141 | 12/1967 | Hoffmann et al. | 5/603 |
| 3,423,773 | 1/1969 | Yamate | 297/377 |
| 3,848,278 | 11/1974 | Propst | 5/603 |
| 4,218,788 | 8/1980 | Steckmesser | 297/377 |
| 4,441,221 | 4/1984 | Enste et al. | 297/464 |
| 4,898,185 | 2/1990 | Fuller | 297/DIG. 6 |
| 4,977,630 | 12/1990 | Oswalt et al. | 5/655 |

FOREIGN PATENT DOCUMENTS 641771  7/1962  Italy ...................................... 297/433

Primary Examiner—Kenneth J. Dorner
Assistant Examiner—Cassandra L. Hope
Attorney, Agent, or Firm—Morton J. Rosenberg; David I. Klein

[57] ABSTRACT

An infant support and restraint system (10) includes a base platform (14) adapted to be mounted on a base surface (16). A first planar member (28) is rotatably adjustable with respect to the base platform (14) through an adjustable support mechanism (26). A second planar member (30) and a third planar member (32) are similarly angularly adjustable with respect to the base platform (14) to allow an infant (12) to be positioned in a physiological position on the infant support and restraint system (10). A first and second pad member (78 and 82) is releasably secured to the first planar member (28) and the second and third planar members (30 and 32). Pad members (78 and 82) may be removed subsequent to a surgical procedure for cleaning or storage purposes. A head support member (88) is releasably secured to the combination of the first planar member (28) and the first pad member (78). Additionally, a torso restraint strap (98) and a pair of leg constraint straps (102 and 102') are releasably securable to the infant support and restraint system (10). In this mmaner, there is provided a modular support and restraint system (10) which maintains the infant in a physiological position during a surgical procedure and reduces the discomfort level of the infant 12).

17 Claims, 4 Drawing Sheets

INFANT SUPPORT AND RESTRAINT SYSTEM

BACKGROUND OF THE INVENTION

1. Field of the Invention

This invention relates to infant support and restraint systems for maintaining an infant in a predetermined position during a surgical procedure. In particular, this invention directs itself to an infant support and restraint system particularly useful in circumcision type surgical procedures. More in particular, this invention directs itself to a support and restraint system for infants which allows the infant to be restrained in a physiological position. More in particular, this invention directs itself to an infant support and restraint system which allows for adjustability of supporting members in both a longitudinal direction as well as varying angular relations. Still further, this invention relates to an infant support and restraint system which provides for releasably secured constraining members and support members which may be removed from the overall infant support and restraint system base frame for cleaning and/or storage.

2. Prior Art

Support and restraint systems are known in the surgical field. The best prior art known to Applicant includes U.S. Pat. Nos. 2,475,003; 2,671,442; 2,743,974; 2,867,483; 2,995,407; 3,215,834; 3,227,440; 3,452,977; 4,318,538; 4,367,869; 4,474,364; 2,751,268; 4,027,869; 4,030,719; 4,648,142; 4,757,811; and, 1,980,848.

A number of prior art systems are directed to surgical tables having joint mechanisms and base clearances for use with auxiliary apparatus. However, although such surgical tables may assume a variety of flex positions, such do not generally have padded strap members for constraint and removable securement mechanisms as is provided in the subject invention concept.

In some surgical table prior art systems such as that shown in U.S. Pat. No. 3,452,977, the tables do comprise a platform divided into interconnected sections however, such sections do not provide the adjustability and rotatability of the subject invention system as described in this invention concept for the purposes and objectives of maintaining an infant in a predetermined positional location during a surgical procedure. Other prior art systems such as that shown in U.S. Pat. Nos. 3,215,834; 2,743,974; and, 2,995,407 are directed to infant surgical boards having straps for immobilizing an infant however such do not allow for the adjustability mechanisms of the subject invention concept as herein described.

SUMMARY OF THE INVENTION

An infant support and restraint system is provided which includes a substantially planar, longitudinally extending base platform for contiguous interface with a base surface. A mechanism is provided for adjustably supporting the infant on the base platform in a plurality of infant support positions. Mechanisms are provided for releasably constraining the infant to the adjustable support mechanism.

An object of the subject invention concept is to allow an infant to be held in a physiological position during a surgical procedure for flexion at the hips and knees and abduction at the hips.

A further object of the subject invention concept is to provide an infant support and restraint system where the infant's head and trunk are elevated to varying inclinations by an adjustable hinge mechanism to minimize the possibility of regurgitation.

A still further object of the subject invention is to provide an infant support and restraint system where the infant's head and trunk are maintained in a predetermined position by a molded padded cushion.

Still further, an object of the infant support and restraint system is to provide a soft elastic band constraint for the infant's trunk which attaches to the main frame by a Velcro type attachment system.

DESCRIPTION OF THE PREFERRED EMBODIMENTS

Figure 1:
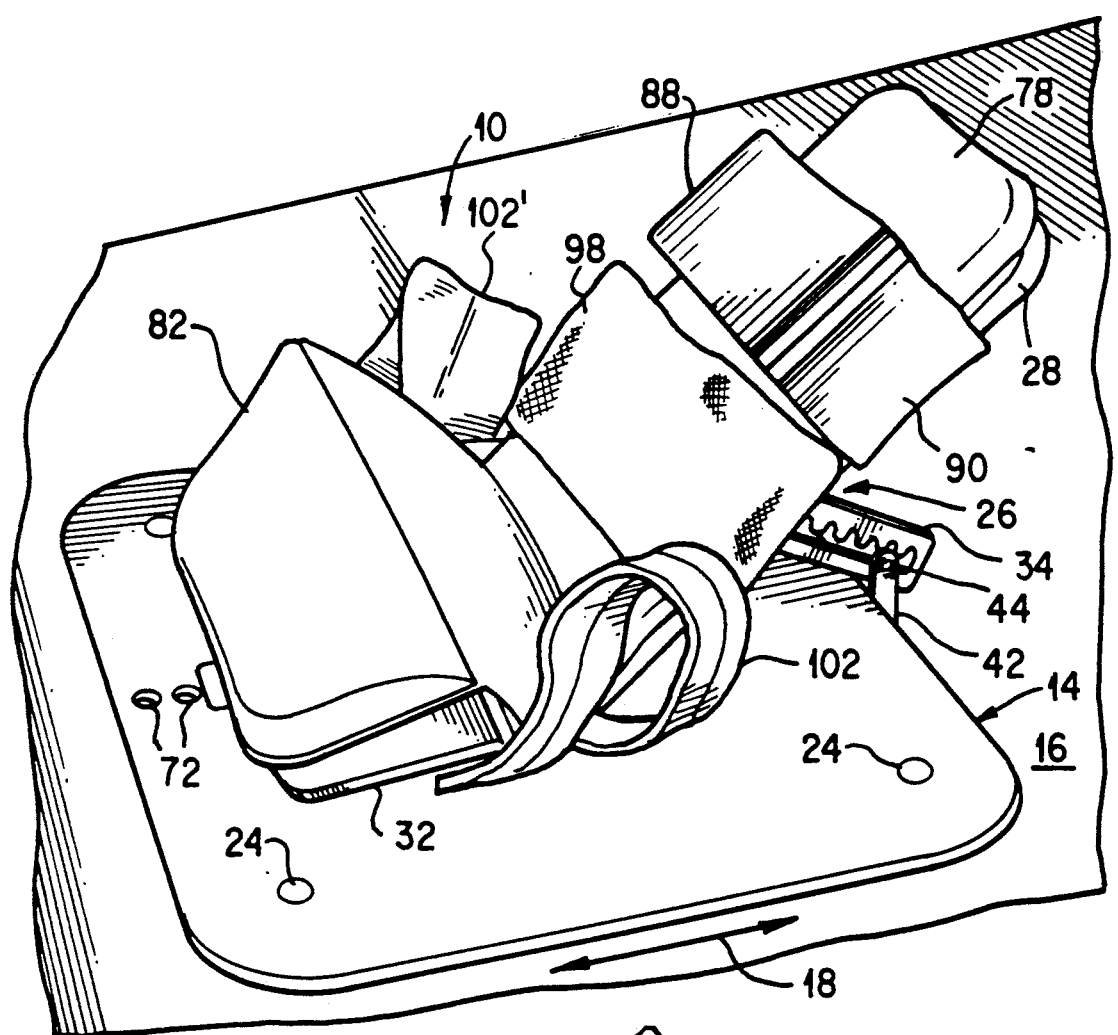
FIG. 1 is a perspective view of the infant support and restraint system mounted on a base surface.
Figure 8:
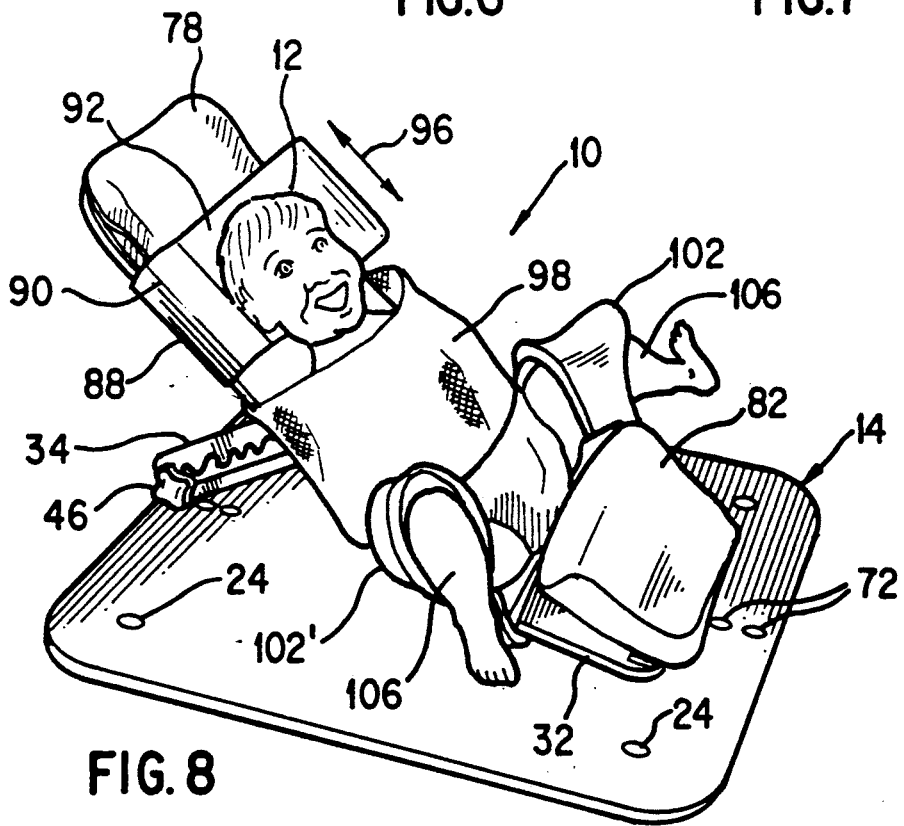
FIG. 8 is a perspective view of the infant support and restraint system showing an infant mounted thereon in preparation of a surgical procedure; and, FIG. 9 is a perspective rear view of the infant support and restraint system.
Figure 9:
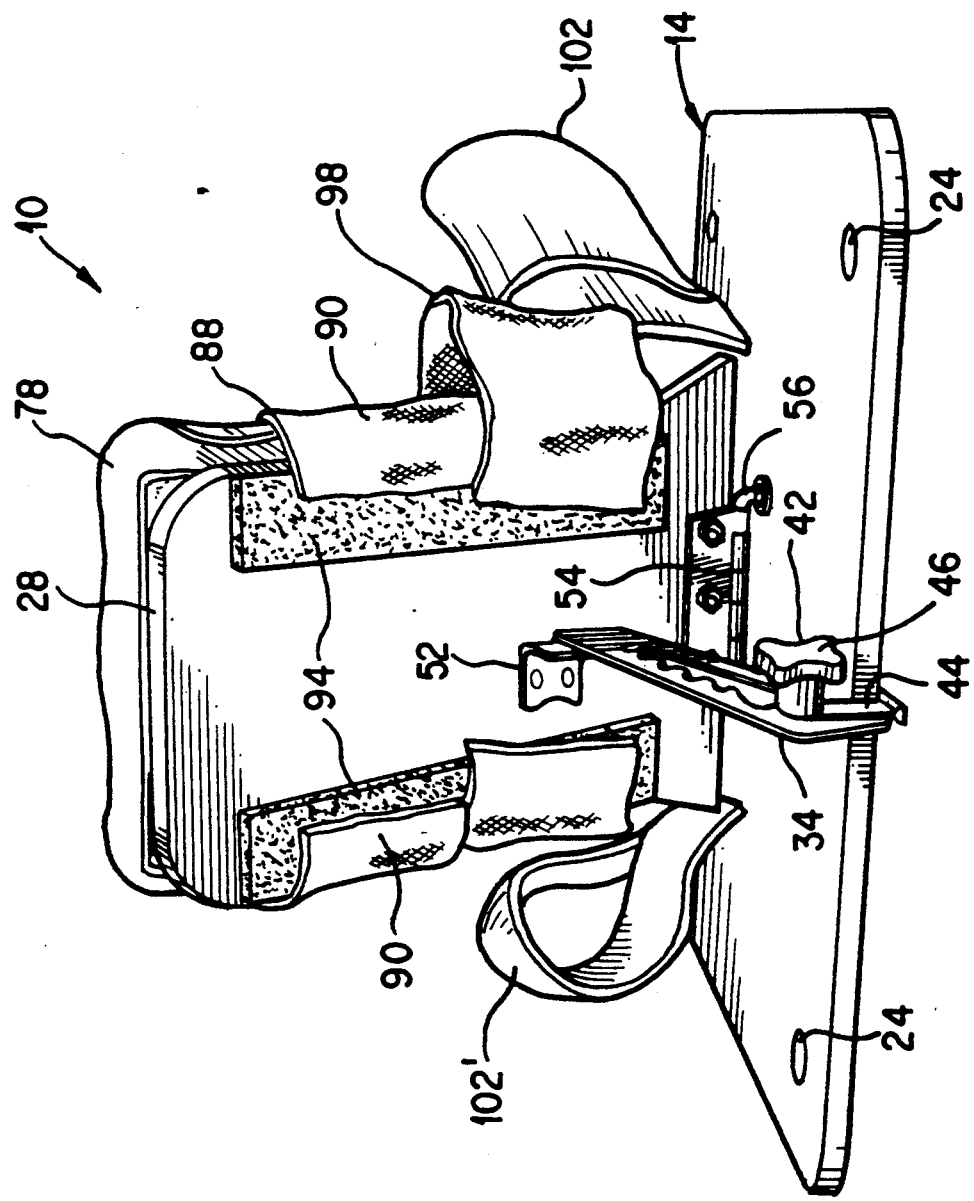

Referring now to FIGS. 1, 8 and 9 there is shown infant support and restraint system 10 for supporting and releasably constraining infant 12 thereon. System 10 may be used for a wide variety of surgical procedures however, it is particularly adaptable to infant circumcisions in order to reduce the stress and discomfort of the infant during the procedure.

Infant support and restraint system 10 includes substantially planar base platform 14 for contiguous interface with base surface 16 as is shown in FIG. 1. Base platform 14 extends in longitudinal direction 18 and provides a mounting surface for remaining elements to be described in following paragraphs. Base platform 14 may be formed of a plastic material not important to the inventive concept as herein described with the exception that base platform 14 is structurally supportive of the loads to be applied. In general, base platform 14 is formed of a closed cell plastic material which may be a PVC composition and easily cleaned subsequent to a particular procedure being performed.

Additionally, base platform 14 provides an additional weight base to lower the center of gravity of the overall infant support and restraint system 10 which may be a factor due to the fact that infant 12 constrained thereon may very well cause dynamic loads which would tend to tip or provide for an unstable condition. Base platform 14 further includes foot members 20 generally but not necessarily mounted at the four corners of rectangularly shaped base platform 14. Foot members 20 may be formed of a high friction plastic material or rubber to increase the frictional contact between the foot members 20 and base surface 16. In this manner there is provided a low center of gravity system having high frictional contact with base surface 16 to increase the overall stability of the system during a particular procedure being performed. Foot members 20 may include extension foot lugs 22 which may be force-fit into openings 24 formed through base platform 14. In this manner, foot members 20 are secured to base platform 14 in a known manner.

Figure 3:
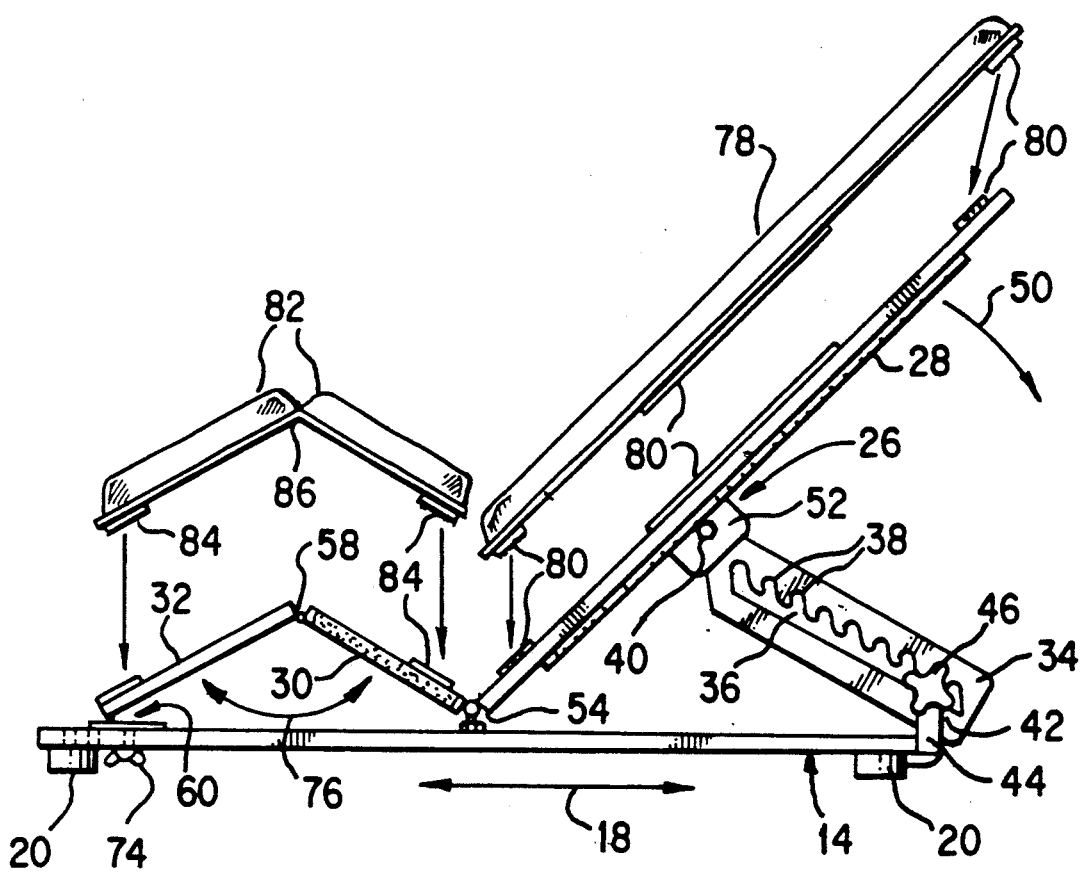
FIG. 3 is an elevational exploded view of the infant support and restraint system showing first and second flexible support members to be releasably secured to the frame section of the infant support and restraint system.

Referring to FIGS. 1 and 3, infant support and restraint system 10 includes adjustable support mechanism 26 for adjustably supporting infant 12 on base platform 14 in a plurality of infant support positions. Adjustable support mechanism 26 includes first substantially planar member 28 which is rotatably secured to base platform 14. Additionally, system 10 includes a second substantially planar member 30 which is rotatably secured to first planar member 28 and further rotatably secured to base platform 14. Third planar member 32 clearly seen in FIG. 3 is pivotedly coupled to second planar member 30 and is releasably securable to base platform 14 at predetermined longitudinally displaced positional locations on base platform 14 as will be described in following paragraphs.

System 10 includes a mechanism for rotatably securing first planar member 28 to base platform 14 and includes extended bar member 34 as shown in FIG. 3 with bar member 34 having a through passage 36 including slot formations 38. Extended bar member 34 is rotatably coupled to first planar member 28 through pivot 40 and is coupled to base platform 14 on an opposing end through locking mechanism 42. As is seen clearly in FIGS. 3 and 9, locking mechanism 42 includes vertical bar member 44 which is secured to base platform 14 through threaded bolts, welding or some like technique not important to the inventive concept with the exception that vertical bar member 44 is rigidly secured to base platform 14. Vertical bar member 44 may include a transverse lug member insertable within one of the slots 38 and is frictionally secured to extended bar member 34 by rotatable hand wheel member 46.

Figure 2:
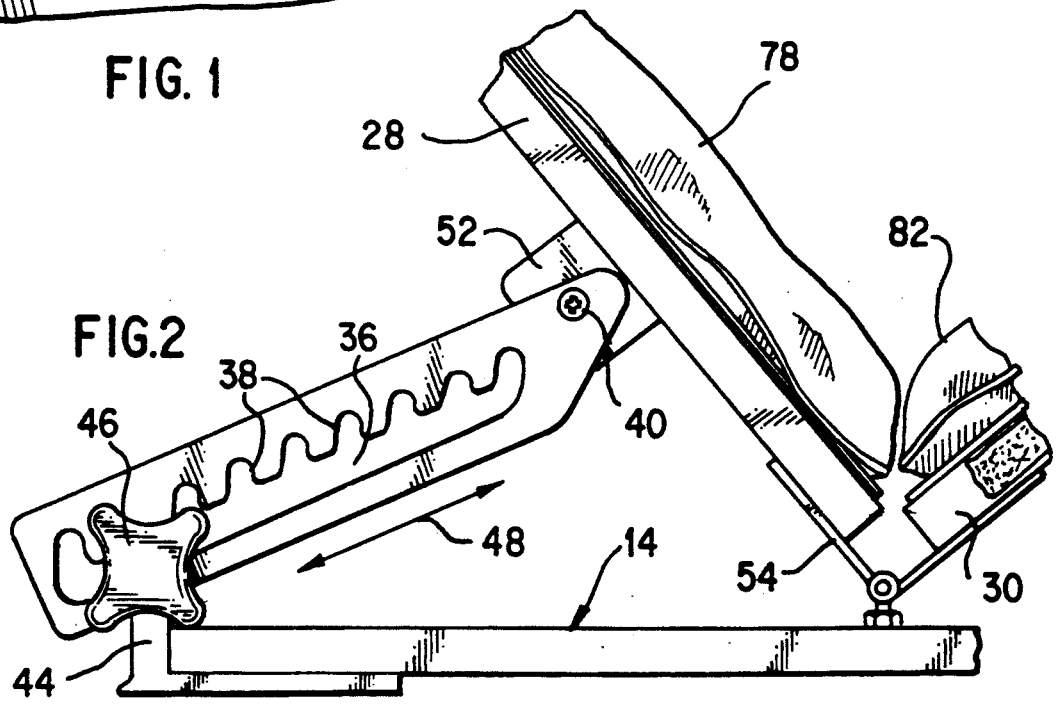
FIG. 2 is an elevational, cutaway view of the angularly adjustable mechanism for angularly adjusting a first planar member with respect to a base platform.

In this manner, rotatable hand wheel 46 and vertical bar member 44 having the transversely directed lug member may be moved or displaced within through passage 36 in the direction of reversible direction arrow 48 as shown in FIG. 2 to provide rotational actuation of first planar member 28 in the direction of arcuate directional arrow 50 shown in FIG. 3. In this manner, locking member 42 may be insertable into one of discretely located slots 38 and frictionally engaged with extended bar member 34 to lockingly secure extended bar member 34 and first planar member 28 to base platform 14. First planar bracket member 52 shown in FIGS. 2, 3 and 9 is fixedly secured to a back surface of first planar member 28 through bolting or some like technique not important to the inventive concept. Pivot member 40, previously described, extends through bracket 52 and passes through extended bar member 34 to allow rotational displacement therebetween.

First hinge member 54 includes first hinge member legs 56 which may be bolted or otherwise secured to base platform 14 as is clearly seen in FIG. 9. In this manner, hinge member 54 is secured to a back surface of first planar member 24 and second planar member 30 to allow rotational displacement therebetween while maintaining fixed securement to base platform 14. Additionally, second hinge member 58 couples second planar member 30 to third planar member 32 in rotative displacement each with respect to the other. Second hinge member 58 is of conventional construction and similar to a standard type hinge mechanism as was described for first hinge member 54.

Figure 4:
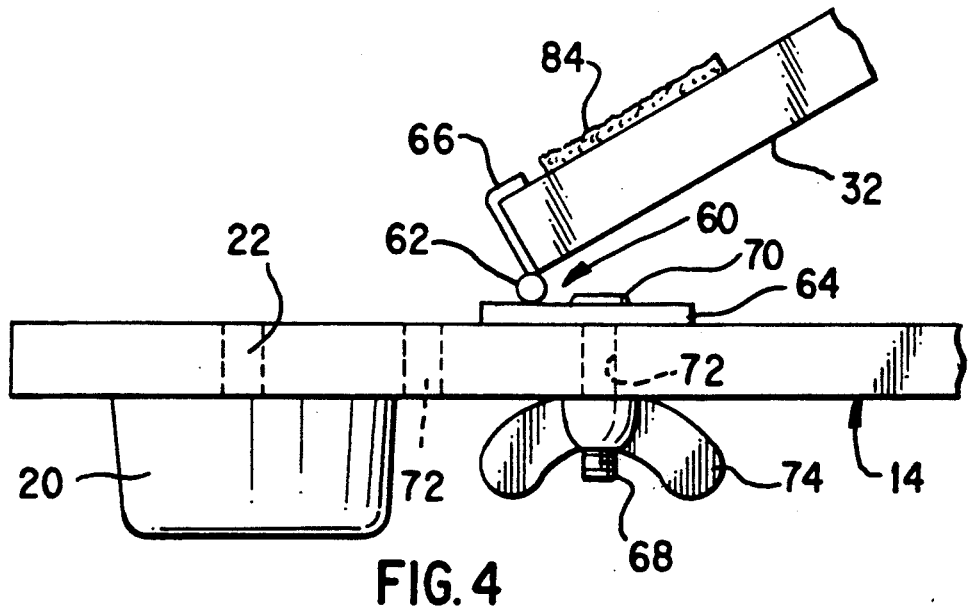
FIG. 4 is an elevational, cutaway view of a section of the base platform showing the longitudinal and angular adjustment mechanism for the third planar member.

System 10 further includes angular and longitudinally positioning mechanism 60 to angularly and longitudinally position third planar member 32 with respect to base platform 14 in fixed securement thereto. As is more clearly seen in FIG. 4, angular and longitudinal positioning mechanism 60 includes third hinge member 62 which includes hinge bottom plate 64 adapted to interface with an upper surface of base platform 14. Third hinge member side plate 66 is fixedly secured to third planar member 32 through bolting, adhesive or some like mechanism not important to the inventive concept as herein described. Locking bolt 68 having locking bolt head 70 passes through base platform 14 within locking bolt openings 72 formed through base platform 14 at discrete locations to allow longitudinal adjustability of third planar member 32. Wing nut 74 is threadedly secured to locking bolt 68 and third hinge member plate 64 is captured between locking bolt head 70 and an upper surface of base platform 14 to maintain a fixed securement of third planar member 32 to base platform 14. By removal of wing nut 74 and insertion of locking bolt 68 in another discretely located opening 72, third planar member 32 and second planar member 30 may be rotatably adjusted and rotatably displaceable in the reversible rotative direction shown by arcuate arrow 76 of FIG. 3.

In this manner, first planar member 28 may be angularly adjustable with respect to base platform 14 while simultaneously second planar member 30 and third planar member 32 may be angularly adjusted each with respect to the other and with respect to base platform 14. Additionally, second and third planar members 30 and 32 may be adjusted in longitudinal direction 18 with respect to base platform 14. The adjustability of the concatenation of adjusting elements allows for differing infant positions to be maintained and aids in the comfort and the diminishment of the discomfort during any surgical procedure.

Support and restraint system 10 further includes first flexible support or pad member 78 which is releasably securable to first planar member 28. First flexible support member 78 is adapted for contiguously interfacing with the body of the infant. First flexible support or pad member 78 may be formed of a molded plastic padded cushion to provide comfort to the infant during the procedure. Additionally, first pad member securement mechanism 80 is formed on an upper surface of first planar member 28 and on a lower surface of first pad member 78. Releasable securement mechanism 80 may include a hook and loop fastening member such as Velcro to allow releasable attachment therebetween. Thus, as is shown in FIG. 3, first pad member 78 may be releasably secured to first planar member 28. Subsequent to the procedure, first pad member 78 may be removed from first planar member 28 to allow for cleaning and subsequent use.

As shown in FIG. 3, there is provided second flexible support or pad member 82 which interfaces with second and third planar members 30 and 32. Second flexible support member 82 may include a crease section 86 to allow for flexible movement between differing sections of second flexible support member 82. Crease section 86 allows for second flexible support member 82 to contiguously interface with planar members 30 and 32 during adjustable rotation therebetween. Additionally, there is provided second pad member releasable securement mechanism 84 which is mounted to an underside of second pad member 82 and an upper surface of each of second and third planar members 30 and 32. In this manner, second flexible support member 82 may be removed subsequent to the procedure in the same manner as was described for first flexible support or pad member 78. Additionally, securement mechanism 84 may be a Velcro type fastener which provides for fixed securement between second pad member 82 and planar members 30 and 32 during the surgical procedure.

Referring now to FIGS. 1, 8 and 9, there is shown head support member 88 having a pair of head support strap members 90 extending on opposing sides of head support central section 92 for releasable securement to a back surface of first planar member 28 as is seen in FIG. 9. Central section 92 of head support member 88 is trough-shaped in cross-sectional contour. Hook and loop strips of the Velcro type are secured to a back surface of first planar member 28 as is seen in FIG. 9. Strips 94 may be adhesively secured to the back surface of first planar member 28 or otherwise fixedly secured thereto. Head support straps 90 have cooperating hook and loop members which releasably secure to strips 94 to provide releasable securement of head support member 88 to the combination of the first planar member 28 and the first flexible support or pad member 78. As can be seen in FIG. 10, head support member 88 may be adjusted in extended direction 96 to allow for differing-sized infants and cooperation for alignment with the head of the infant within head support member 88. As was the case for first and second flexible support or pad members 78 and 82, head support member 88 may be formed of a molded padded type cushion to allow flexibility and comfort for the infant when being supported in the infant support and restraint system 10. Subsequent to the surgical procedure being performed, strap members 90 of head support member 88 may be released from securement with extended strip members 94 for cleaning and/or storage until the next procedure.

Figures 5, 6, 7:
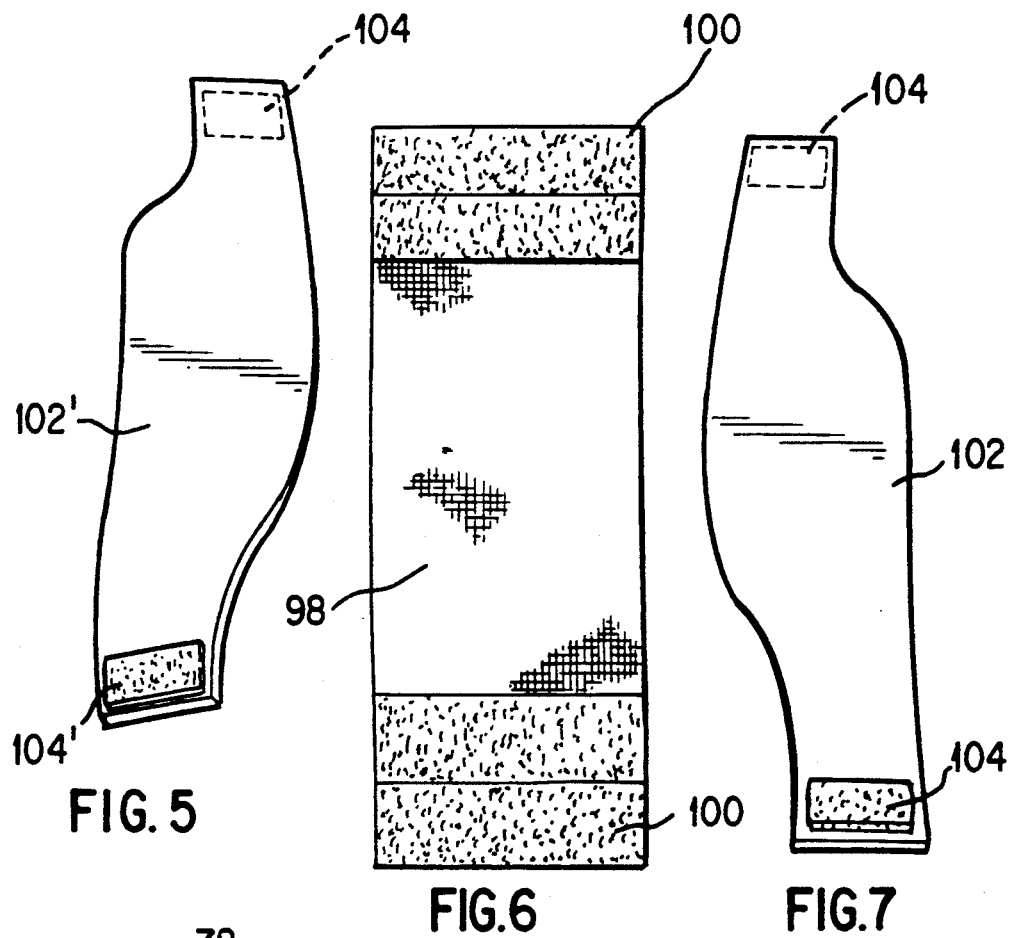
FIG. 5 is a plan view of a limb constraint strap showing a releasable securement mechanism secured on opposing sides thereof.
FIG. 6 is a plan view of a torso restraint strap showing a releasable securement mechanism formed on opposing ends.
FIG. 7 is a second leg strap constraint member.

Referring now to FIGS. 6 and 8, there is shown torso constraint strap member 98 for constraining the torso of the infant to first planar member 28. Torso constraint strap 98 includes opposing end sections 100 having formed thereon a Velco-type hook and loop fastener 100 which interfaces and releasably secures to extended hook and loop strips 94 shown in FIG. 9 mounted on a back surface of first planar member 28. In this manner, the torso of the infant is releasably constrained to first planar member 28.

Further included in infant support and restraint system 10 as shown in FIGS. 5, 7 and 8 is limb or leg constraint straps 102, 102'. Each of straps 102, 102' includes limb constraint releasable securement sections 104, 104' formed on opposing sides of each of limb constraint straps 102 and 102'. Limb constraint releasable securement sections 104 and 104' are adapted to interface with the rear surfaces of second and third planar members 30 and 32 which have cooperating Velcro-like hook and loop fasteners to maintain infant 12 in an abduction position during the surgical procedure. Leg straps 102 and 102' encircle a portion of the legs of infant 12 to maintain positional relation of infant legs 106 in a predetermined position during the procedure.

As shown in FIG. 8, the arms of infant 12 may be maintained beneath torso or trunk constraint strap 98. However, in normal operation, the arms of infant 12 may be left free to move without disturbing the surgical field. The strap member 98 may be located beneath the armpits of infant 12 to allow some freedom of movement by infant 12 during the procedure.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended Claims.

What is claimed is:
1. An infant support and restraint system comprising:
 (a) a substantially planar, longitudinally extending base platform for contiguous interface with a base surface;
 (b) means for adjustably supporting said infant on said base platform in a plurality of infant support positions, said means for adjustably supporting said infant including (1) a first substantially planar member having one end rotatably secured to said base platform by a first pivotal connection, (2) a second substantially planar member having a first end rotatably secured to said first substantially planar member and said base platform by said first pivotal connection, and (3) a third substantially planar member having a first end pivotally coupled to a second end of said second substantially planar member and a second end rotatably coupled to said base platform by a second pivotal connection, said second pivotal connection being releasably securable to said base platform at predetermined longitudinally displaced positional locations on said base platform; and,
 (c) means for releasably constraining said infant to said adjustable support means, said means for releasably constraining including a pair of leg constraint strap members, each of said pair of leg strap members encircling a portion of a leg of said infant and being releasably secured to said second and third substantially planar members on opposing ends of said leg strap members.

2. The infant support and restraint system as recited in claim 1 includes:
 (a) an extended bar member having discretely located slots formed therethrough, said extended bar member being pivotally coupled to said first substantially planar member on one end thereof; and,
 (b) a locking member secured to said base platform and insertable into one of said discretely located slots for locking securement to said extended bar member.

3. The infant support and restraint system as recited in claim 1 including a first hinge member fixedly secured to said base platform, said first hinge member being rotatably coupled to said first and second substantially planar members for providing rotative displacement each with respect to the other.

4. The infant support and restraint system as recited in claim 1 including a second hinge member for coupling said second and third substantially planar members in rotative displacement each with respect to the other.

5. The infant support and restraint system as recited in claim 1 including:
(a) a first flexible support member releasably securable to said first substantially planar member, said first flexible support member for contiguously interfacting with said infant; and,
(b) means for releasably securing said first flexible support member to said first substantially planar member, said releasable securement means including hook and loop fastening members secured to said first flexible support member and said first substantially planar member in cooperating relation therewith.

6. The infant support and restraint system as recited in claim 5 wherein said first flexible support member is a cushioning pad for contacting the torso and head of said infant.

7. The infant support and restrain system as recited in claim 1 including:
(a) a second flexible support member releasably securable to said second and third substantially planar members, said second flexible support member for contiguously interfacing with said infant; and,
(b) means for releasably securing said second flexible support member to said second and third substantially planar members.

8. The infant support and restraint system as recited in claim 1 including an infant head support member releasably secured to said first subtantially planar member.

9. The infant support and restraint system as recited in claim 8 where said infant head support member includes a central section and a pair of head support strap members extending on opposing sides therefrom for releasable securement to a back surface of said first substantially planar member.

10. The infant upport and restraint system as recited in claim 9 where said infant head support member includes a flexible trough shaped central section.

11. The infant support and restraint system as recited in claim 9 including means for releasably securing said head support member to said back surface of said first substantially planar member.

12. The infant support and restraint system as recited in claim 11 where said means for releasably securing said head support member includes cooperating hook and loop fastening members mounted on said back surface of said first substantially planar member and said head support strap members.

13. The infant support and restraint system as recited in claim 1 where said means for constraining said infant to said adjustable support means includes means for releasably constraining the torso of said infant to said first substantially planar member.

14. The infant support and restraint system as recited in claim 13 where said releasable constraint means includes a torso strap member releasably securable to a back surface of said first substantially planar member.

15. An infant support and restraint system comprising:
(a) a substantially planar, longitudinally extending base platform for contiguous interface with a base surface.
(b) means for adjustably supporting said infant on said base platform in a plurality of infant support positions, said means for adjustably supporting said infant including (1) a first substantially planar member rotatably secured to said base platform, (2) a second substantially planar member rotatably secured to said first substantially planar member and said base platform, and (3) a third substantially planar member pivotally coupled to said second substantially planar member and releasably securable to said base platform at predetermined longitudinally displaced positional locations on said base platform;
(c) means for realeasably constraining said infant to said adjustable support means; and,
(d) means for angularly and longitudinally positioning said third substantially planar member with respect to said platform in fixed securement thereto, said angular and longitudinal positioning means including (1) a locking bolt insertable through a predetermined through opening formed in said base platform, said locking bolt having a locking bolt head, and (2) a third hinge member rotatably secured to said third substantially planar member and fixedly secured to said base platform in captured relation between said locking bolt head and said base platform.

16. The infant support and restraint system as recited in claim 15 including means for releasably constraining the limbs of said infant to said second and third substantially planar members.

17. The infant support and restraint system as recited in claim 16 where said limb constraining means includes a pair of releasably securable leg straps encircling a portion of the legs of said infant and secured on opposing ends to said second and third substantially planar members by hook and loop fasteners.

* * * * *